United States Patent
Baehner et al.

(10) Patent No.: US 10,654,886 B2
(45) Date of Patent: *May 19, 2020

(54) METHOD FOR SEPARATION OF MONOMERIC POLYPEPTIDES FROM AGGREGATED POLYPEPTIDES

(71) Applicant: HOFFMANN-LA ROCHE INC., Little Falls, NJ (US)

(72) Inventors: Monika Baehner, Munich (DE); Adelbert Grossmann, Eglfing (DE); Stefan Hepbildikler, Penzberg (DE)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/707,888

(22) Filed: Sep. 18, 2017

(65) Prior Publication Data

US 2018/0094023 A1 Apr. 5, 2018

Related U.S. Application Data

(63) Continuation of application No. 14/127,085, filed as application No. PCT/EP2012/062570 on Jun. 28, 2012, now Pat. No. 9,783,570.

(30) Foreign Application Priority Data

Jul. 1, 2011 (EP) ..................................... 11172348

(51) Int. Cl.
| | | |
|---|---|---|
| *C07K 1/36* | (2006.01) | |
| *G01N 30/02* | (2006.01) | |
| *C07K 1/16* | (2006.01) | |
| *C07K 1/18* | (2006.01) | |
| *C07K 1/20* | (2006.01) | |
| *C07K 14/54* | (2006.01) | |

(52) U.S. Cl.
CPC ............... *C07K 1/165* (2013.01); *C07K 1/18* (2013.01); *C07K 1/20* (2013.01); *C07K 1/36* (2013.01); *C07K 14/5443* (2013.01); *C07K 2319/30* (2013.01)

(58) Field of Classification Search
CPC .................................. C07K 1/36; G01N 30/02
See application file for complete search history.

(56) References Cited

U.S. PATENT DOCUMENTS

| | | | |
|---|---|---|---|
| 5,231,178 A | | 7/1993 | Holtz et al. |
| 5,331,095 A | * | 7/1994 | Shadle .................. C07K 14/503 530/399 |
| 5,429,746 A | | 7/1995 | Shadle et al. |
| 7,691,980 B2 | | 4/2010 | Gagnon |
| 7,834,152 B2 | | 11/2010 | Strom et al. |
| 9,422,329 B2 | | 8/2016 | Falkenstein et al. |
| 9,783,570 B2 | * | 10/2017 | Baehner .................. C07K 1/18 |
| 2008/0167450 A1 | | 7/2008 | Pan |
| 2010/0069617 A1 | | 3/2010 | Gagnon |
| 2010/0311952 A1 | | 12/2010 | Falkenstein et al. |
| 2011/0129468 A1 | * | 6/2011 | Mccue ............... C07K 14/7151 424/134.1 |
| 2012/0123002 A1 | | 5/2012 | Shinohara et al. |
| 2013/0005948 A1 | | 1/2013 | Binder et al. |
| 2014/0243508 A1 | | 8/2014 | Falkenstein et al. |
| 2015/0018241 A1 | | 1/2015 | Falkenstein et al. |

FOREIGN PATENT DOCUMENTS

| | | |
|---|---|---|
| JP | 2007525501 A | 9/2007 |
| JP | 2008505851 A | 2/2008 |
| JP | 2008542218 A | 11/2008 |
| JP | 2010517942 A | 5/2010 |
| JP | 2010158624 A | 7/2010 |
| JP | 2010528076 A | 8/2010 |
| JP | 2011514895 A | 5/2011 |
| WO | WO 2005042569 A1 | 5/2005 |
| WO | WO 2005082483 A1 | 9/2005 |
| WO | WO 2005082926 A1 | 9/2005 |
| WO | WO 2005100394 A2 | 10/2005 |
| WO | WO 2006125599 A2 | 11/2006 |
| WO | WO 2008086335 A2 | 7/2008 |
| WO | WO 2008087184 A2 | 7/2008 |
| WO | WO 2008145351 A1 | 12/2008 |
| WO | WO 2009111347 A1 | 9/2009 |
| WO | WO 2011001963 A1 | 1/2011 |

OTHER PUBLICATIONS

Aldington et al., "Scale-up of monoclonal antibody purification processes", J Chromatogr B Analyt Technol Biomed Life Sci., 848(1):64-78 (2007).

Gagnon, "How to choose an industrial cation exchanger for IgG purification", BioProcess International, 4(9):22-34 (even pages are only presented in this article) (2010).

(Continued)

*Primary Examiner* — Karen Cochrane Carlson

(57) ABSTRACT

Herein is reported a method for obtaining a polypeptide in monomeric form comprising the steps of a) providing a solution comprising the polypeptide in monomeric form and in aggregated form, wherein the ratio of monomeric to aggregated form is 4:1 or less as determined by size exclusion chromatography, b) performing a mixed-mode chromatography in bind-and-elute mode, or a hydrophobic interaction chromatography in flow-through mode, or a size-exclusion chromatography, and c) performing a weak cation exchange chromatography in bind-and-elute mode or flow-through mode, and thereby obtaining the polypeptide in monomeric form.

13 Claims, 5 Drawing Sheets

Specification includes a Sequence Listing.

(56) References Cited

OTHER PUBLICATIONS

Gagnon, "IgG aggregate removal by charged-hydrophobic mixed mode chromatography", Curr Pham Biotechnol, 10(4):434-439 (2009).
Liu et al., "Recovery and purification process development for monoclonal antibody production", Mabs, 2(5):480-499 (2010).
Tornoe et al., "Pilot scale purification of human monoclonal IgM (COU-1) for clinical trials", J Immunol Methods., 205(1):11-17 (1997).

* cited by examiner

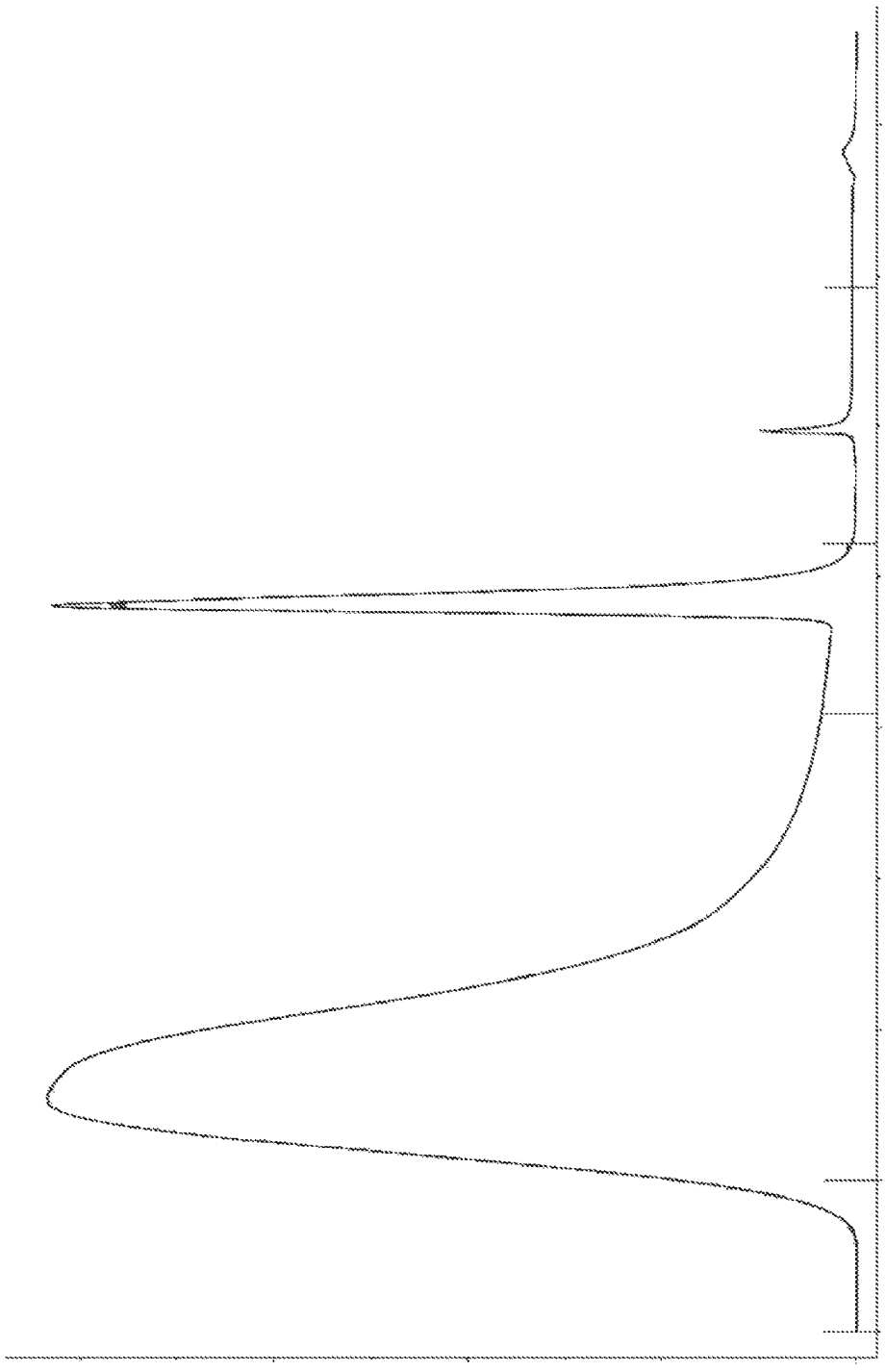

SEQUENCE LISTING

<160> NUMBER OF SEQ ID NOS: 2

<210> SEQ ID NO 1
<211> LENGTH: 1113
<212> TYPE: DNA
<213> ORGANISM: Artificial Sequence
<220> FEATURE:
<223> OTHER INFORMATION: nucleic acid sequence of the human mutated
      IL15/Fc with CD5 leader peptide

<400> SEQUENCE: 1

```
atgcccatgg ggtctctgca accgctggcc accttgtacc tgctggggat gctggtcgct    60
tcctgcctcg gaaactgggt gaatgtaata agtgatttga aaaaaattga agatcttatt   120
caatctatgc atattgatgc tactttatat acggaaagtg atgttcaccc cagttgcaaa   180
gtaacagcaa tgaagtgctt tctcttggag ttacaagtta tttcacttga gtccggagat   240
gcaagtattc atgatacagt agaaaatctg atcatcctag caaacaacag tttgtcttct   300
aatgggaatg taacagaatc tggatgcaaa gaatgtgagg aactggagga aaaaaatatt   360
aaagaatttt tggacagttt tgtacatatt gtcgacatgt tcatcaacac ttcggatccc   420
aaatctgctg acaaaactca cacatgccca ccgtgcccag cacctgaact cctgggggga   480
ccgtcagtct tcctcttccc cccaaaaccc aaggacaccc tcatgatctc ccggacccct   540
gaggtcacgt gcgtggtggt ggacgtgagc cacgaagacc ctgaggtcaa gttcaactgg   600
tacgtggacg gcgtggaggt gcataatgcc aagacaaagc cgcgggagga gcagtacaac   660
agcacgtacc gtgtggtcag cgtcctcacc gtcctgcacc aggactggct gaatggcaag   720
gagtacaagt gcaaggtctc caacaaagcc ctcccagccc ccatcgagaa aaccatctcc   780
aaagccaaag ggcagccccg agaaccacag gtgtacaccc tgcccccatc ccgggatgag   840
ctgaccaaga accaggtcag cctgacctgc ctggtcaaag gcttctatcc agcgacatc    900
gccgtggagt gggagagcaa tgggcagccg gagaacaact acaagaccac gcctcccgtg   960
ctggactccg acggctcctt cttcctctac agcaagctca ccgtggacaa gagcaggtgg  1020
cagcagggga acgtcttctc atgctccgtg atgcatgagg ctctgcacaa ccactacacg  1080
cagaagagcc tctccctgtc tccgggtaaa tga                               1113
```

<210> SEQ ID NO 2
<211> LENGTH: 370
<212> TYPE: PRT
<213> ORGANISM: Artificial Sequence
<220> FEATURE:
<223> OTHER INFORMATION: amino acid sequence of the human mutated
     IL15/Fc with CD5 leader peptide

<400> SEQUENCE: 2

```
Met Pro Met Gly Ser Leu Gln Pro Leu Ala Thr Leu Tyr Leu Leu Gly
1               5                   10                  15

Met Leu Val Ala Ser Cys Leu Gly Asn Trp Val Asn Val Ile Ser Asp
            20                  25                  30

Leu Lys Lys Ile Glu Asp Leu Ile Gln Ser Met His Ile Asp Ala Thr
        35                  40                  45

Leu Tyr Thr Glu Ser Asp Val His Pro Ser Cys Lys Val Thr Ala Met
    50                  55                  60

Lys Cys Phe Leu Leu Glu Leu Gln Val Ile Ser Leu Glu Ser Gly Asp
65                  70                  75                  80

Ala Ser Ile His Asp Thr Val Glu Asn Leu Ile Ile Leu Ala Asn Asn
                85                  90                  95

Ser Leu Ser Ser Asn Gly Asn Val Thr Glu Ser Gly Cys Lys Glu Cys
            100                 105                 110

Glu Glu Leu Glu Glu Lys Asn Ile Lys Glu Phe Leu Asp Ser Phe Val
        115                 120                 125

His Ile Val Asp Met Phe Ile Asn Thr Ser Asp Pro Lys Ser Ala Asp
    130                 135                 140
```

```
Lys Thr His Thr Cys Pro Pro Cys Pro Ala Pro Glu Leu Leu Gly Gly
145                 150                 155                 160

Pro Ser Val Phe Leu Phe Pro Pro Lys Pro Lys Asp Thr Leu Met Ile
                165                 170                 175

Ser Arg Thr Pro Glu Val Thr Cys Val Val Val Asp Val Ser His Glu
            180                 185                 190

Asp Pro Glu Val Lys Phe Asn Trp Tyr Val Asp Gly Val Glu Val His
        195                 200                 205

Asn Ala Lys Thr Lys Pro Arg Glu Glu Gln Tyr Asn Ser Thr Tyr Arg
    210                 215                 220

Val Val Ser Val Leu Thr Val Leu His Gln Asp Trp Leu Asn Gly Lys
225                 230                 235                 240

Glu Tyr Lys Cys Lys Val Ser Asn Lys Ala Leu Pro Ala Pro Ile Glu
                245                 250                 255

Lys Thr Ile Ser Lys Ala Lys Gly Gln Pro Arg Glu Pro Gln Val Tyr
                260                 265                 270

Thr Leu Pro Pro Ser Arg Asp Glu Leu Thr Lys Asn Gln Val Ser Leu
            275                 280                 285

Thr Cys Leu Val Lys Gly Phe Tyr Pro Ser Asp Ile Ala Val Glu Trp
290                 295                 300

Glu Ser Asn Gly Gln Pro Glu Asn Asn Tyr Lys Thr Thr Pro Pro Val
305                 310                 315                 320

Leu Asp Ser Asp Gly Ser Phe Phe Leu Tyr Ser Lys Leu Thr Val Asp
                325                 330                 335

Lys Ser Arg Trp Gln Gln Gly Asn Val Phe Ser Cys Ser Val Met His
            340                 345                 350

Glu Ala Leu His Asn His Tyr Thr Gln Lys Ser Leu Ser Leu Ser Pro
            355                 360                 365

Gly Lys
370
```

METHOD FOR SEPARATION OF MONOMERIC POLYPEPTIDES FROM AGGREGATED POLYPEPTIDES

This application is a continuation of U.S. application Ser. No. 14/127,085, filed on Dec. 17, 2013, which is a U.S. National Stage Application under 35 U.S.C. § 371 of International Patent Application No. PCT/EP2012/062570, filed Jun. 28, 2012, which claims the benefit of priority of European Patent Application No. 11172348.2, filed Jul. 1, 2011, the disclosures of each of which are incorporated by reference herein in their entireties.

This application incorporates by reference the Computer Readable Form (CRF) of a Sequence Listing in ASCII text format submitted via EFS-Web.

Herein is reported a method in the field of the purification of polypeptide preparations with high aggregate content. In more detail the method as reported herein is in the field of the separation of polypeptides in monomeric form from polypeptides in aggregated form. The method is well suited for the purification of crude polypeptide solutions comprising more than 20% of aggregated polypeptide. The purification is achieved by a combination of only two chromatography steps, for example a combination of a first mixed-mode cation exchange chromatography step and a second cation exchange chromatography step.

BACKGROUND OF THE INVENTION

An effective immune response is initiated by T-cells of the immune system being activated, with this activation being induced by an antigen or mitogen. The activation of the T-cells requires a large number of cellular changes, including, for example, the expression of cytokines and their receptors. These cytokines include, inter alia, IL-15 and IL-2. These interleukins are known growth factors which play a significant role in the proliferation and differentiation of human and murine T-cells, macrophages, natural killer (NK) cells, cytotoxic T-cells (CTL), and lymphocyte-activated killer (LAK) cells as well as in the co-stimulation of B cells which have been activated, for example, by anti-immunoglobulin (anti-IgM) or phorbol esters. The proliferation of these cells augments the immune response of an organism.

In a large number of diseases, it is necessary, for therapeutic reasons, to suppress a response of the patient's immune system. These diseases include, for example, autoimmune diseases, in particular diabetes mellitus type I, rheumatoid arthritis, multiple sclerosis, chronic liver diseases, inflammatory intestinal diseases, graft-versus-host disease and transplant rejection. One therapeutic approach is that of using immunosuppressants, in particular antagonistic IL-15 or IL-2 antibodies, or IL-15 or IL-2 antagonists, to suppress the humoral or the cellular immune response.

The above-described IL-15 antagonists are mutated IL-15 (mut-IL-15) sequences which achieved antagonistic effects either on their own or as fusion proteins. These fusion proteins are polypeptides which consist of a N-terminal mut-IL-15 fragment and a C-terminal Fc fragment, in particular a murine IgG2a or human IgG1 (see, e.g., WO 97/41232; WO 2004/035622; Kim, Y. S., et al., J. Immunol. 160 (1998) 5742-5748).

In general the IEP-values (isoelectric point, pI) of proteins are important characteristics for ion exchange chromatography of proteins. Below the IEP proteins gain a positive net charge and can be chromatographed on cation exchangers, above the pI they have a negative net charge and anion exchangers should be used (see e.g. New comprehensive biochemistry, Neuberger, A., and van Deenen, L. L. M. (eds.), Volume 8, Separation Methods, Deyl, Z. (ed.), Elsevier Science Publishers B.V. (1984) page 247).

Conjugated Factor VIII molecules are reported in WO 2009/108806. In US 2009/0304669 a preparative purification process for human furin is reported. A chromatography purification of antibodies is reported in US 2009/270596. In WO 2009/074634 is reported a composition for pulmonary delivery. Polypeptides, antibody variable domains and antagonists are reported in WO 2008/149147. In US 2008/177048 an enhanced capacity and purification of antibodies by mixed-mode chromatography in the presence of aqueous-soluble non-ionic organic polymers is reported. Refolding of recombinant proteins is reported in US 2008/008975. In US 2007/167613 a process for purification of antibodies is reported. Antibody purification is reported in US 2007/112178. Purified immunoglobulin fusion proteins and methods of their purification are reported in WO 2009/111347.

Aldington et al. (J. Chrom. B 848 (2007) 64-78) report the scale-up of monoclonal antibody purification processes. Pilot scale purification of human monoclonal IgM (COU-1) is reported by Tornoe at al. (J. Immunol. Meth. 205 (1997) 11-17). In US 2010/069617 enhanced protein aggregate removal by mixed-mode chromatography on hydrophobic interaction media in the presence of protein-excluded zwitterions is reported.

SUMMARY OF THE INVENTION

Herein is reported a method for purifying a polypeptide or immunoglobulin wherein the starting solution comprises an aggregate content of 20% or more as determined by size exclusion chromatography, i.e. for removing aggregates from a crude polypeptide or immunoglobulin solution with high aggregate content.

The method is especially useful for solutions containing a high aggregate burden of at least 20% as determined by size-exclusion chromatography.

The high aggregate burden can be reduced to low levels with a combination of two chromatography steps. It has been found that a combination of two chromatography steps provides for improved aggregate removal and at the same time for an increased recovery compared to a single chromatography step for the purification of crude polypeptide or immunoglobulin solution comprising more than 20% of the polypeptide or immunoglobulin in aggregated form.

It has been found that a mixed-mode chromatography material and a weak cation exchange chromatography material can be operated at pH values above, i.e. higher than, the isoelectric point (IEP) of the polypeptide of interest in order to obtain the polypeptide in monomeric form, i.e. in order to separate it from the polypeptide in aggregated form.

One aspect as reported herein is a method for producing a polypeptide in monomeric form, i.e. a monomeric polypeptide, comprising the steps a) i) applying a solution comprising the polypeptide in monomeric form and in aggregated form, wherein the aggregated form is 20% or more as determined by size exclusion chromatography of the total polypeptide in the solution, to a hydrophobic interaction chromatography material and recovering the polypeptide from the flow-through, or ii) applying a solution comprising the polypeptide in monomeric form and in aggregated form, wherein the aggregated form is 20% or more as determined by size exclusion chromatography of the total polypeptide in the solution, to a mixed-mode chromatography material and recovering the polypeptide from the mixed-mode chromatography material, and b) applying the solution obtained in the previous step to a weak cation exchange chromatography material and recovering the polypeptide therefrom and thereby producing the polypeptide in monomeric form, i.e. the monomeric polypeptide.

In one embodiment the pH value of the solution prior to the application to the mixed-mode chromatography material or the weak cation exchange chromatography material is adjusted to a value at least 0.2 pH units above the isoelectric point (IEP) of the polypeptide.

In one embodiment the recovering from the weak cation exchange chromatography material is from the eluate of the weak cation exchange chromatography material or from the flow-through of the weak cation exchange chromatography material.

In one embodiment the step of applying the solution to a hydrophobic interaction chromatography material comprises the following steps applying to the hydrophobic interaction chromatography material a solution comprising Tris buffer with a pH value of about 7.0, of from about 0.5 mol/l to about 1.5 mol/l sodium chloride and of from about 10% to about 15% (v/v) 2-propanol, adjusting the solution comprising the polypeptide prior to the applying to the chromatography material to a pH value of about 7.0, a sodium chloride concentration of from about 0.5 mol/l to about 1.5 mol/l and a 2-propanol content of from about 10% to about 15% (v/v), applying the adjusted solution comprising the polypeptide to the hydrophobic interaction chromatography material.

In one embodiment the applying to and recovering from the mixed-mode chromatography material comprises the following steps applying to the mixed-mode chromatography material a solution comprising a buffer with a pH value of the IEP of the polypeptide plus about 0.7 pH units to about 1.3 pH units, adjusting the solution comprising the polypeptide or immunoglobulin prior to the applying to the mixed-mode chromatography material to a pH value of the IEP of the polypeptide or the immunoglobulin, respectively, plus about 0.7 pH units to about 1.3 pH units, applying the adjusted solution comprising the polypeptide or immunoglobulin to the mixed-mode chromatography material, recovering the polypeptide from the mixed-mode chromatography material by applying a solution comprising a phosphate buffer with a pH value of the IEP of the polypeptide plus about 1.7 pH units to about 2.3 pH units.

In one embodiment the applying to the weak cation exchange chromatography material and the recovering of the polypeptide or immunoglobulin therefrom comprises the following steps applying to the weak cation exchange chromatography material a solution comprising an acetate buffer with a pH value of the IEP of the polypeptide plus about 0.2 pH units to about 1.0 pH units, adjusting the solution comprising the polypeptide or immunoglobulin prior to the applying to the chromatography material to a pH value of the IEP of the polypeptide or the immunoglobulin, respectively, plus about 0.2 pH units to about 1.0 pH units, applying the adjusted solution comprising the polypeptide or immunoglobulin to a weak cation exchange chromatography material, recovering the polypeptide or immunoglobulin from the weak cation exchange chromatography material by applying a solution comprising sodium chloride or potassium chloride at a concentration of from about 210 mmol/l to about 240 mmol/l, or recovering the polypeptide or immunoglobulin from the weak cation exchange chromatography material with a solution of a pH value of from about pH 6.0 to about pH 8.0.

In one embodiment the recovering is at a pH value of about pH 5.0 and the sodium chloride concentration is about 230 mmol/l, or the recovering is at a pH value of about pH 5.2 and the sodium chloride concentration is about 210 mmol/l.

In one embodiment the applying to the weak cation exchange chromatography material and the recovering of the polypeptide or the immunoglobulin therefrom comprises the following steps applying to the weak cation exchange chromatography material a solution with a pH value of the IEP of the polypeptide or immunoglobulin, respectively, plus about 0.2 pH units to about 1.2 pH units, adjusting the solution comprising the polypeptide or immunoglobulin prior to the applying to the chromatography material to a pH value of the IEP of the polypeptide or immunoglobulin, respectively, plus about 0.2 pH units to about 1.2 pH units, applying the adjusted solution to a weak cation exchange chromatography material, recovering the polypeptide or immunoglobulin from the flow-through.

In one embodiment the concentration of the buffer is less than 150 mmol/l and more than 1 mmol/l.

In one embodiment the adjusting is to an acetate buffer of about pH 5.1 of from about 100 mmol/l to about 120 mmol/l, or to an acetate buffer of about pH 5.5 and of about 40 mmol/l to about 55 mmol/l, or to an acetate buffer of about pH 6.0 and of about 10 mmol/l.

In one embodiment the buffer is selected from citrate buffer, acetate buffer and MES buffer.

In one embodiment the recovering is by an isocratic elution. In one embodiment each recovering is by an isocratic elution.

In one embodiment the buffer has a conductivity of about 1.9 mS/cm.

In one embodiment the buffer in step ii) is an acetate buffer of about pH 5.3 and of about 50 mmol/l to about 75 mmol/l, or an acetate buffer of about pH 5.5 and of about 7.5 mmol/l to about 15 mmol/l.

In one embodiment the recovering is by adding 10% (v/v) of an acetate buffer of a pH value of from about pH 6.0 to about pH 6.5 or the recovering is by adding 60% (v/v) of a MES buffer of a pH value of about pH 8.0.

In one embodiment the mixed-mode chromatography material is Capto MMC, the hydrophobic interaction chromatography material is selected from phenyl sepharose and butyl sepharose, or the weak cation exchange chromatography material is a carboxy-methyl sepharose or Toyopearl CM-650.

In one embodiment the polypeptide comprises an Fc-part and the first step prior to step a) is applying the solution to a protein A chromatography material and recovering the polypeptide. In one embodiment the recovering is with an acidic buffer.

In one embodiment the polypeptide is an immunoglobulin, or an immunoglobulin fusion, or an immunoglobulin Fc-region fusion polypeptide. In one embodiment the polypeptide is a polypeptide-Fc-region fusion polypeptide wherein the polypeptide is fused to the N-terminus of the Fc-region.

In one embodiment the polypeptide has the amino acid sequence of SEQ ID NO: 02.

All embodiments as reported herein can be combined in any combination.

DETAILED DESCRIPTION OF THE INVENTION

Herein is reported a method for purifying a polypeptide or immunoglobulin, i.e. for the removing of aggregates from a crude polypeptide or immunoglobulin solution. This method is especially useful for solutions containing a high aggregate burden of at least 20% as determined by size-exclusion chromatography.

One aspect as reported herein is a method for producing a polypeptide in monomeric form comprising the steps
   a) (i) applying a solution, which comprises the polypeptide in monomeric form and in aggregated form, wherein the aggregated form is 20% or more of the total polypeptide in the solution as determined by size exclusion chromatography, to a mixed-mode chromatography material and recovering the polypeptide from the mixed-mode chromatography material, or
      (ii) applying a solution, which comprises the polypeptide in monomeric form and in aggregated form, wherein the aggregated form is 20% or more of the total polypeptide in the solution as determined by size exclusion chromatography, to a hydrophobic interaction chromatography material and recovering the polypeptide in the flow-through of the hydrophobic interaction chromatography material,
   and
   b) (i) applying the solution obtained in step a) comprising the polypeptide to a weak cation exchange chromatography material and recovering and thereby producing the polypeptide in monomeric form from the weak cation exchange chromatography material, or
      (ii) applying the solution obtained in step a) comprising the polypeptide to a weak cation exchange chromatography material and recovering and thereby producing the polypeptide in monomeric from in the flow-through of the weak cation exchange chromatography material.

It has been found that a mixed-mode chromatography material and a weak cation exchange chromatography material can be operated at pH values above, i.e. higher than, the isoelectric point (IEP) of the polypeptide of interest in order to obtain the polypeptide in monomeric form, i.e. in order to separate it from the polypeptide in aggregated form.

The method as reported herein can be applied to any Fc-region containing polypeptide, such as antibodies, antibody fusion polypeptides or Fc-region fusion polypeptides, and only minor, product-specific modifications are required based on the isoelectric point (pI) of the polypeptide which can be determined and performed by a person skilled in the art without undue burden using the information provided herein. By the method as reported herein the choice of parameters required for a new molecule of interest is guided and reduced and the method can be put into practice with only minor requirements for product specific adaptation.

The method as reported herein comprises a unique combination of chromatography steps with a defined mode (bind-and-elute, flow-through).

The method as reported herein is
   suitable for sterile manufacturing, and
   simple, e.g. no preparative size exclusion chromatography required, no linear gradient elution required, and
   cost efficient, e.g. process steps yields, low cost of chromatography materials, small amount of chromatography material required, low concentration of salts, low burden of waste treatment due to kind and concentration of employed salts, and
   a low volume process, e.g. due to the use of low salt concentration solutions extensive dilution or buffer exchange steps can be omitted, and
   scaleable, e.g. due to relatively high binding capacities and/or load densities, respectively, in the chromatography steps required column volumes can be kept small and easy-to-handle in manufacturing scale, and
   not requiring high concentrations of corrosive compounds, such as sodium chloride.

The term "in monomeric form" denotes that a polypeptide or immunoglobulin, respectively, is not associated with further polypeptides or immunoglobulins, respectively, i.e. neither covalently nor non-covalently. The term "in monomeric form" does not necessarily denote that 100% of the molecule is present in monomeric form. It furthermore denotes that the molecule is essentially in monomeric form, i.e. at least 90% of the molecule are in monomeric from, or at least 95% of the molecule are in monomeric form, or at least 98% of the molecule are in monomeric form, or at least 99% of the molecule are in monomeric form, or more than 99% of the molecule are in monomeric form.

The term "in aggregated form" denotes that a polypeptide or an immunoglobulin, respectively, is associated, either covalently or non-covalently, with further, i.e. at least one, polypeptides or immunoglobulins, respectively, and which can be identified by analytical size exclusion chromatography or by SDS-polyacrylamide electrophoresis under non-reducing conditions and can be separated from the monomeric form. The term "in aggregated form" does not necessarily denote that 100% of the molecule is present in aggregated form. It furthermore denotes that an molecule is essentially in aggregated form, i.e. at least 90% of the molecule are in aggregated from, or at least 95% of the molecule are in aggregated form, or at least 98% of the molecule are in aggregated form, or at least 99% of the molecule are in aggregated form, or more than 99% of the molecule are in aggregated form.

The term "about" denotes that the thereafter following value is no exact value but is the center point of a range that is +/−10% of the value, or +/−5% of the value, or +/−2% of the value, or +/−1% of the value. If the value is a relative value given in percentages the term "about" also denotes that the thereafter following value is no exact value but is the center point of a range that is +/−10% of the value, or +/−5% of the value, or +/−2% of the value, or +/−1% of the value, whereby the upper limit of the range cannot exceed a value of 100%.

The term "mixed-mode chromatography" denotes a chromatographic method employing a binding mechanism based on both ionic and hydrophobic interactions between the mixed-mode chromatography material and the polypeptide or immunoglobulin, respectively. A mixed-mode chromatography material comprises a ligand for binding of molecules based on both types of interaction. An "ionic interaction" between the chromatography material and the polypeptide or immunoglobulin, respectively, is established under conditions of an "ion exchange chromatography". A "hydrophobic interaction" is established under conditions of a "hydrophobic interaction chromatography". The term "hydrophobic interaction material" denotes a high molecular weight matrix used as immobile stationary phase comprising covalently bound hydrophobic residues. The "hydrophobic interaction chromatography material" can bind hydrophobic molecules at high ionic strength and in absence of hydrophobic solvents in the mobile phase. Thereby, a polypeptide is able to bind to the "hydrophobic interaction chromatography material" employing its hydrophobic parts. The binding is reduced by decreasing the ionic strength of the mobile phase on the addition of solvents, chaotropic agents or detergents to the mobile phase or on decreasing the temperature. The bound polypeptides or immunoglobulins are released into the mobile phase. In addition to the bind-and-elute mode the hydrophobic chromatography can be performed in a "flow-through mode". The term "flow-through mode" denotes a chromatography mode wherein the conditions are chosen in a way that the polypeptide in monomeric form remains in the mobile phase whereas the polypeptide in aggregated form and impurities are bound to the hydrophobic interaction material. Depending on the nature of the hydrophobic ligand the "hydrophobic interaction material" is referred to as, e.g. "phenyl" or "butyl" or "Capto MMC" resin. The Capto MMC resin carries a ligand which contains a phenyl group for hydrophobic interaction as well as a carboxyl group for ionic interaction.

The term "weak cation exchange chromatography" denotes a chromatographic method employing a "weak cation exchange material". The term "ion exchange material" as used within this application denotes an immobile high molecular weight matrix that carries covalently bound charged substituents used as stationary phase in ion exchange chromatography. For overall charge neutrality not covalently bound counter ions are bound thereto. The "ion exchange material" has the ability to exchange its not covalently bound counter ions for similarly charged ions of the surrounding solution. Depending on the charge of its exchangeable counter ions the "ion exchange material" is referred to as "cation exchange material" or as "anion exchange material". Depending on the nature of the charged group (substituent) the "ion exchange material" is referred to as, e.g. in the case of cation exchange resins, sulfonic acid resin (S), or sulfopropyl resin (SP), or carboxymethyl resin (CM). Depending on the chemical nature of the charged group/substituent the "ion exchange material" can additionally be classified as strong or weak ion exchange resin, depending on the strength of the covalently bound charged substituent. For example, strong cation exchange resins have a sulfonic acid group, such as a sulfopropyl group, as charged substituent, whereas weak cation exchange materials have a carboxylic group, such as a carboxymethyl group, as charged substituent. In one embodiment the weak cation exchange chromatography material is a carboxymethyl cation exchange chromatography material, i.e. a chromatography material that comprises carboxymethyl groups.

The term "mutIL15-Fc" denotes a fusion polypeptide consisting of an N-terminal mutated or non-mutated IL-15 part and a C-terminal Fc-part. This fusion polypeptide was available in sufficient quantities in our laboratory and has been used as an example and should not be construed to limit the scope of the invention which is defined by the appended claims. In one embodiment the polypeptide or immunoglobulin is a fusion polypeptide of an interleukin-15 part and an Fc-part of human origin of SEQ ID NO: 1 or 2. Such a molecule is reported in example 1 and SEQ ID NO: 3 and 4 (with murine Fc part) of WO 2005/100394.

The term "Fc-region" denotes the part of an immunoglobulin that is not involved directly in binding to the immunoglobulin's binding partner, but exhibit various effector functions. Depending on the amino acid sequence of the constant region of the heavy chains, immunoglobulins are divided in the classes: IgA, IgD, IgE, IgG, and IgM. Some of these classes are further divided into subclasses (isotypes), i.e. IgG in IgG1, IgG2, IgG3, and IgG4, or IgA in IgA1 and IgA2. According to the class to which an immunoglobulin belongs the heavy chain constant regions of immunoglobulins are called α (IgA), δ (IgD), ε (IgE), γ (IgG), and μ (IgM), respectively. An "Fc-region" of an immunoglobulin is a term well known to the skilled artisan and defined on basis of the papain cleavage of full length immunoglobulins. In one embodiment the polypeptide or immunoglobulin is a fusion polypeptide comprising a human Fc-region or an Fc-region derived from human origin.

The term "bind-and-elute mode" denotes an operation mode of a purification method, in which a solution containing a substance of interest to be purified is brought in contact with a stationary phase, preferably a solid phase, whereby the substance of interest binds to the stationary phase. As a result the substance of interest is retained on the stationary phase whereas substances not of interest are removed with the flow-through or the supernatant. The substance of interest is afterwards eluted from the stationary phase in a second step and thereby recovered from the stationary phase with an elution solution.

The term "buffered solution" denotes a solution in which changes of pH due to the addition or release of acidic or alkaline substances is leveled by the dissolved buffer substance. Any buffer substance with such properties can be used. Generally pharmaceutically acceptable buffers substances are used. In one embodiment the buffered solution is selected from a phosphate buffered solution consisting of phosphoric acid and/or salts thereof, or an acetate buffered solution consisting of acetic acid and salts thereof, or a citrate buffered solution consisting of citric acid and/or salts thereof, or a morpholine buffered solution, or a 2-(N-morpholino) ethanesulfonic buffered solution, or a histidine buffered solution, or a glycine buffered solution, or a tris (hydroxymethyl) aminomethane (TRIS) buffered solution. In another embodiment the buffer solution is selected from a phosphate buffered solution, or an acetate buffered solution, or a citrate buffered solution, or a histidine buffered solution. Optionally the buffered solution may comprise an additional salt, such as e.g. sodium chloride, sodium sulphate, potassium chloride, potassium sulfate, sodium citrate, or potassium citrate.

The term "immunoglobulin conjugate" denotes a polypeptide comprising at least one domain of an immunoglobulin heavy or light chain conjugated via a peptide bond to a further polypeptide. The further polypeptide can be a non-immunoglobulin peptide, such as a hormone, or toxin, or growth receptor, or antifusogenic peptide, or complement factor, or the like.

The term "flow-through mode" denotes an operation mode of a purification method, in which a solution containing a substance of interest, e.g. an immunoglobulin in monomeric form, to be purified is brought in contact with a stationary, preferably solid, phase whereby the substance of interest does not bind to that stationary phase. As a result the substance of interest is obtained either in the flow-through (if the purification method is a chromatographical method) or the supernatant (if the purification method is a batch method). Substances not of interest, e.g. an immunoglobulin in aggregated form, which were also present in the solution bind to the stationary phase and are in that way removed from the solution. This does not necessarily denote that 100% of the substances not of interest are removed from the solution but essentially 100% of the substances not of interest are removed, i.e. at least 50% of the substances not of interest are removed from the solution, preferably at least 75% of the substances not of interest are removed the from solution, preferably at least 90% of the substances not of interest are removed from the solution, preferably more than 95% of the substances not of interest are removed from the solution.

In a single chromatographic purification step employing either a mixed-mode cation exchange chromatography material or a cation exchange chromatography material the removal of the aggregated polypeptide concomitantly with an acceptable or even high recovery cannot be achieved. That is, in order to obtain sufficient aggregate removal a reduction of the recovery has to be accepted.

It has been found that a combination of two chromatography steps provides for improved aggregate removal and at the same time for an increased recovery compared to a single chromatography step for the purification of crude polypeptide or immunoglobulin solution comprising more than 20% of the polypeptide or immunoglobulin in aggregated form.

One aspect as reported herein is a method for removing a polypeptide or an immunoglobulin in aggregated form from the polypeptide or immunoglobulin in monomeric form comprising the following steps
  a) providing a solution comprising the polypeptide in monomeric form and in aggregated form, wherein the aggregated form is 20% or more as determined by size exclusion chromatography of the total polypeptide or immunoglobulin in the solution,
  b) applying the solution to a mixed-mode chromatography material in bind-and-elute mode, or to a hydrophobic interaction chromatography material in flow-through mode and recovering the polypeptide or immunoglobulin, and
  c) applying the solution obtained in the previous step to a weak cation exchange chromatography material in bind-and-elute mode or flow-through mode and recovering the polypeptide or immunoglobulin, and thereby obtaining the polypeptide or the immunoglobulin in monomeric form and removing the polypeptide or immunoglobulin in aggregated form.

In one embodiment the pH value of the solution applied to the mixed-mode chromatography material and/or the weak cation exchange chromatography material is at least 0.2 pH units above the isoelectric point of the polypeptide.

In one embodiment the concentration of the buffer is less than 150 mmol/l and more than 1 mmol/l.

The term "applying to" denotes a partial step of a chromatography method in which a solution containing a substance of interest to be purified is brought in contact with a chromatography material. This denotes that a) the solution is added to a chromatographic device in which the chromatography material is located, or b) that the chromatography material is added to the solution. In case a) the solution containing the substance of interest to be purified passes through the chromatography material allowing for an interaction between the chromatography material and the substances in solution. Depending on the conditions, such as e.g. pH, conductivity, salt concentration, temperature, and/or flow rate, some substances of the solution are bound to the chromatography material and, thus, are removed from the solution. Other substances remain in solution. The substances remaining in solution can be found in the flow-through. The "flow-through" denotes the solution obtained after the passage of the chromatographic device, which may either be the applied solution containing the substance of interest or the buffer, which is used to flush the column or to cause elution of one or more substances bound to the chromatography material. In one embodiment the chromatographic device is a column, or a cassette. The substance of interest can be recovered from the solution after the purification step by methods familiar to a person of skill in the art, such as e.g. precipitation, salting out, ultrafiltration, diafiltration, lyophilization, affinity chromatography, or solvent volume reduction to obtain the substance of interest in substantially homogeneous form. In case b) the chromatography material is added, e.g. as a solid, to the solution containing the substance of interest to be purified allowing for an interaction between the chromatography material and the substances in solution. After the interaction the chromatography material is removed, e.g. by filtration, and the substance of interest is either bound to the chromatography material and removed therewith from the solution or not bound to the chromatography material and remains in the solution.

In one embodiment the weak cation exchange chromatography step is performed in flow-through mode. In another embodiment the weak cation exchange chromatography is performed at a pH value in a range of up to 2.5 pH unit above the isoelectric point of the polypeptide. In one embodiment the polypeptide is a fusion polypeptide comprising an immunoglobulin Fc-region. In another embodiment the polypeptide is an immunoglobulin.

The method as reported herein is exemplified in the following using a fusion polypeptide consisting of an IL-15 variant and a human immunoglobulin Fc-region. This is presented solely as an example and has not to be construed as a limitation. The true scope is set forth in the claims.

The crude cultivation supernatant comprising the fusion polypeptide in monomeric and in aggregated form can be purified with a combination of different chromatography steps. With a chromatography on recombinant protein A (e.g. MabSelectSuRe) a solution comprising more than 20% of the fusion polypeptide, i.e. about 30%, as soluble aggregate (as determined by SEC) is obtained. With a chromatography on MabSelectXtra a solution comprising about 40% to 50% of the fusion polypeptide as soluble aggregate is obtained.

In one embodiment after step a) and prior to step b) the solution is applied to a protein A affinity chromatography material in bind-and-elute mode and recovered from the protein A affinity chromatography material.

The solution applied to the mixed-mode chromatography material or to the hydrophobic interaction chromatography material comprises about 20%, in another embodiment about 30%, and in a further embodiment about 40% of the polypeptide or immunoglobulin in aggregated form.

In one embodiment the polypeptide or immunoglobulin is recovered from the protein A affinity chromatography material by applying an acidic citrate buffered solution.

Specific Embodiments of the Invention

1. A method for producing a polypeptide in monomeric form comprising the steps
    a) i) applying a solution comprising the polypeptide in monomeric form and in aggregated form, wherein the aggregated form is 20% or more as determined by size exclusion chromatography of the total polypeptide in the solution, to a hydrophobic interaction chromatography material and recovering the polypeptide from the flow-through, or
    ii) applying a solution comprising the polypeptide in monomeric form and in aggregated form, wherein the aggregated form is 20% or more as determined by size exclusion chromatography of the total polypeptide in the solution, to a mixed-mode chromatography material and recovering the polypeptide from the mixed-mode chromatography material,
    and
    b) applying the solution obtained in the previous step to a weak cation exchange chromatography material and recovering the polypeptide therefrom and thereby producing the polypeptide in monomeric form.
2. The method according to embodiment 1, characterized in that the solution applied to the mixed-mode chromatography material and/or the weak cation exchange chromatography material has a pH value at least 0.2 pH units and at most 2.5 pH units above the isoelectric point of the polypeptide.
3. The method according to any one of the preceding embodiments, characterized in that the solution applied to the mixed-mode chromatography material and/or the weak cation exchange chromatography material is a buffered solution with a buffer concentration of from 1 mmol/l to 150 mmol/l.
4. The method according to any one of the preceding embodiments, characterized in that the recovering from the weak cation exchange chromatography material is from the eluate of the weak cation exchange chromatography material.
5. The method according to any one of embodiments 1 to 3, characterized in that the recovering from the weak cation exchange chromatography materials is from the flow-through of the weak cation exchange chromatography material.
6. The method according to any one of the preceding embodiments, characterized in that the applying the solution to a hydrophobic interaction chromatography material comprises the following steps
    applying to the hydrophobic interaction chromatography material a solution comprising a buffer with a pH value of about 7.0, of from about 0.5 mol/l to about 1.5 mol/l sodium chloride and of from about 10% to about 15% (v/v) 2-propanol,
    adjusting the solution comprising the polypeptide prior to the applying to the chromatography material to a pH value of about 7.0, a sodium chloride concentration of from about 0.5 mol/l to about 1.5 mol/l and a 2-propanol content of from about 10% to about 15% (v/v),
    applying the adjusted solution comprising the polypeptide to a hydrophobic interaction chromatography material.
7. The method according to embodiment 6, characterized in that the buffer is a Tris buffer.
8. The method according to any one of the preceding embodiments, characterized in that the applying to and recovering from the mixed-mode chromatography material comprises the following steps
    applying to the mixed-mode chromatography material a solution comprising a buffer with a pH value of the IEP of the polypeptide plus about 0.7 pH units to about 1.3 pH units,
    adjusting the solution comprising the polypeptide prior to the applying to the chromatography material to a pH value of the IEP of the polypeptide plus about 0.7 pH units to about 1.3 pH units,
    applying the adjusted solution comprising the polypeptide to a mixed-mode chromatography material,
    recovering the polypeptide from the mixed-mode chromatography material by applying a solution comprising a phosphate buffer with a pH value of the IEP of the polypeptide plus about 1.7 pH units to about 2.3 pH units.
9. The method according to any one of the embodiments 1 to 7, characterized in that the applying to and recovering from the mixed-mode chromatography material comprises the following steps
    applying to the mixed-mode chromatography material a solution comprising acetate buffer with a pH value of about pH 5.5,
    adjusting the solution comprising the polypeptide prior to the applying to the chromatography material to a pH value of about pH 5.5,
    applying the adjusted solution to a mixed-mode chromatography material,
    recovering the polypeptide from the mixed-mode chromatography material by applying a solution comprising a phosphate buffer with a pH value of about pH 6.5.
10. The method according to any one of the preceding embodiments, characterized in that the applying to the weak cation exchange chromatography material and the recovering from the weak cation exchange chromatography material comprises the following steps
    applying to the weak cation exchange chromatography material a solution comprising a buffer with a pH value of the IEP of the polypeptide plus about 0.2 pH units to about 1.0 pH units,
    adjusting the solution comprising the polypeptide prior to the applying to the chromatography material to a pH value of the IEP of the polypeptide plus about 0.2 pH units to about 1.0 pH units,
    applying the adjusted solution comprising the polypeptide to a weak cation exchange chromatography material,
    recovering the polypeptide from the weak cation exchange chromatography material by applying a solution comprising sodium chloride or potassium chloride at a concentration of from about 210 mmol/l to about 240 mmol/l, or
    recovering the polypeptide from the weak cation exchange chromatography material with a solution of a pH value of from about pH 6.0 to about pH 8.0.
11. The method according to embodiment 8, characterized in that the applying to the weak cation exchange chromatography material and the recovering from the weak cation exchange chromatography material comprises the following steps
    applying to the weak cation exchange chromatography material a solution comprising a buffer with a pH value of from about pH 5.0 to about pH 5.4,
    adjusting the solution comprising the polypeptide prior to the applying to the chromatography material to a pH value of from about pH 5.0 to about pH 5.4,
    applying the adjusted solution to a weak cation exchange chromatography material, recovering the polypeptide from the weak cation exchange chromatography material by applying a solution comprising sodium chloride or potassium chloride at a concentration of from about 100 mmol/l to about 230 mmol/l, or recovering the polypeptide from the weak cation exchange chromatography material with a solution of a pH value of from about pH 6.0 to about pH 8.0.

12. The method according to embodiment 10 or 11, characterized in that in the recovering the pH value is about pH 5.0 and the sodium chloride concentration is about 230 mmol/l, or the pH value is about pH 5.2 and the sodium chloride concentration is about 210 mmol/l.

13. The method according to any one of the preceding claims, characterized in that the applying to the weak cation exchange chromatography material and the recovering from the weak cation exchange chromatography material comprises the following steps applying to the weak cation exchange chromatography material a solution comprising a buffer with a pH value of the IEP of the polypeptide plus about 0.2 pH units to about 1.2 pH units, adjusting the solution comprising the polypeptide prior to the applying to the chromatography material to a pH value of the IEP of the polypeptide plus about 0.2 pH units to about 1.2 pH units, applying the adjusted solution to a weak cation exchange chromatography material, recovering the polypeptide from the flow-through.

14. The method according to any one of the preceding embodiments, characterized in that the applying to the weak cation exchange chromatography material and the recovering from the weak cation exchange chromatography material comprises the following steps applying to the weak cation exchange chromatography material a solution comprising a buffer with a pH value of from about pH 5.0 to about pH 5.4, adjusting the solution comprising the polypeptide prior to the applying to the chromatography material to a pH value of from about pH 5.0 to about pH 5.4, applying the adjusted solution to a weak cation exchange chromatography material, recovering the polypeptide from the flow-through.

15. The method according to embodiment 13 or 14, characterized in that the adjusting is to an acetate buffer of about pH 5.1 and of from about 100 mol/l to about 120 mmol/l, or to an acetate buffer of about pH 5.5 and of about 40 mmol/l to about 55 mmol/l, or to an acetate buffer of about pH 6.0 and of about 10 mmol/l.

16. The method according to any one of embodiments 3 to 14, characterized in that the buffer is selected from citrate buffer, acetate buffer and MES buffer.

17. The method according to any one of the preceding embodiments, characterized in that the weak cation exchange chromatography material is a carboxymethyl weak cation exchange chromatography material and that the recovering from the weak cation exchange chromatography materials is from the flow-through of the weak cation exchange chromatography material.

18. The method according to any one of the previous embodiments, characterized in that the weak cation exchange chromatography material is a carboxymethyl weak cation exchange chromatography material, that the buffer used for the weak cation exchange chromatography material is an acetate buffer, and that the recovering from the weak cation exchange chromatography materials is from the flow-through of the weak cation exchange chromatography material.

19. The method according to any one of embodiments 10 to 18, characterized in that the recovering is by an isocratic elution.

20. The method according to any one of embodiments 8 to 19, characterized in that the buffer has a conductivity of about 1.9 mS/cm.

21. The method according to any one of embodiments 8 to 9 and 16 to 20, characterized in that the buffer in step ii) is an acetate buffer of about pH 5.3 and of about 50 mmol/l to about 75 mmol/l, or an acetate buffer of about pH 5.5 and of about 7.5 mmol/l to about 15 mmol/l.

22. The method according to any one of embodiments 10 to 12 and 18 to 21, characterized in that the recovering is by adding 10% (v/v) of an acetate buffer of a pH value of from about pH 6.0 to about pH 6.5 or the recovering is by adding 60% (v/v) of a MES buffer of a pH value of about pH 8.0.

23. The method according to any one of the preceding embodiments, characterized in that the mixed-mode chromatography material is a chromatography material comprising hydrophobic chromatography groups and cation exchange chromatography groups, such as Capto MMC, the hydrophobic interaction chromatography material is selected from phenyl sepharose and butyl sepharose, and/or the weak cation exchange chromatography material is a carboxymethyl cation exchange chromatography material, such as carboxy-methyl sepharose or Toyopearl CM-650.

24. The method according to any one of the preceding embodiments, characterized in that the polypeptide comprises an Fe-part and the first step is a applying the solution to a protein A chromatography material and recovering the polypeptide with an acidic buffer.

25. The method according to any one of the preceding embodiments, characterized in that the polypeptide is an immunoglobulin, or an immunoglobulin fusion, or an immunoglobulin Fc-region fusion.

26. The method according to any one of the preceding embodiments, characterized in that the polypeptide has the amino acid sequence of SEQ ID NO: 02.

The following examples, sequence listing and figures are provided to aid the understanding of the present invention, the true scope of which is set forth in the appended claims. It is understood that modifications can be made in the procedures set forth without departing from the spirit of the invention.

Description of the Sequence Listing

SEQ ID NO: 01 Nucleic acid sequence of human mutated interleukin 15-Fc-region fusion polypeptide.

SEQ ID NO: 02 Amino acid sequence of human mutated interleukin 15-Fc-region fusion polypeptide.

DESCRIPTION OF THE FIGURES

FIGS. 3A-C Sequence of FIG. 3A protein A affinity chromatography in bind-and-elute mode, FIG. 3B mixed-mode chromatography in bind-and-elute mode, and FIG. 3C weak cation exchange chromatography in bind-and-elute mode.

DEFINITIONS

Figure 1:
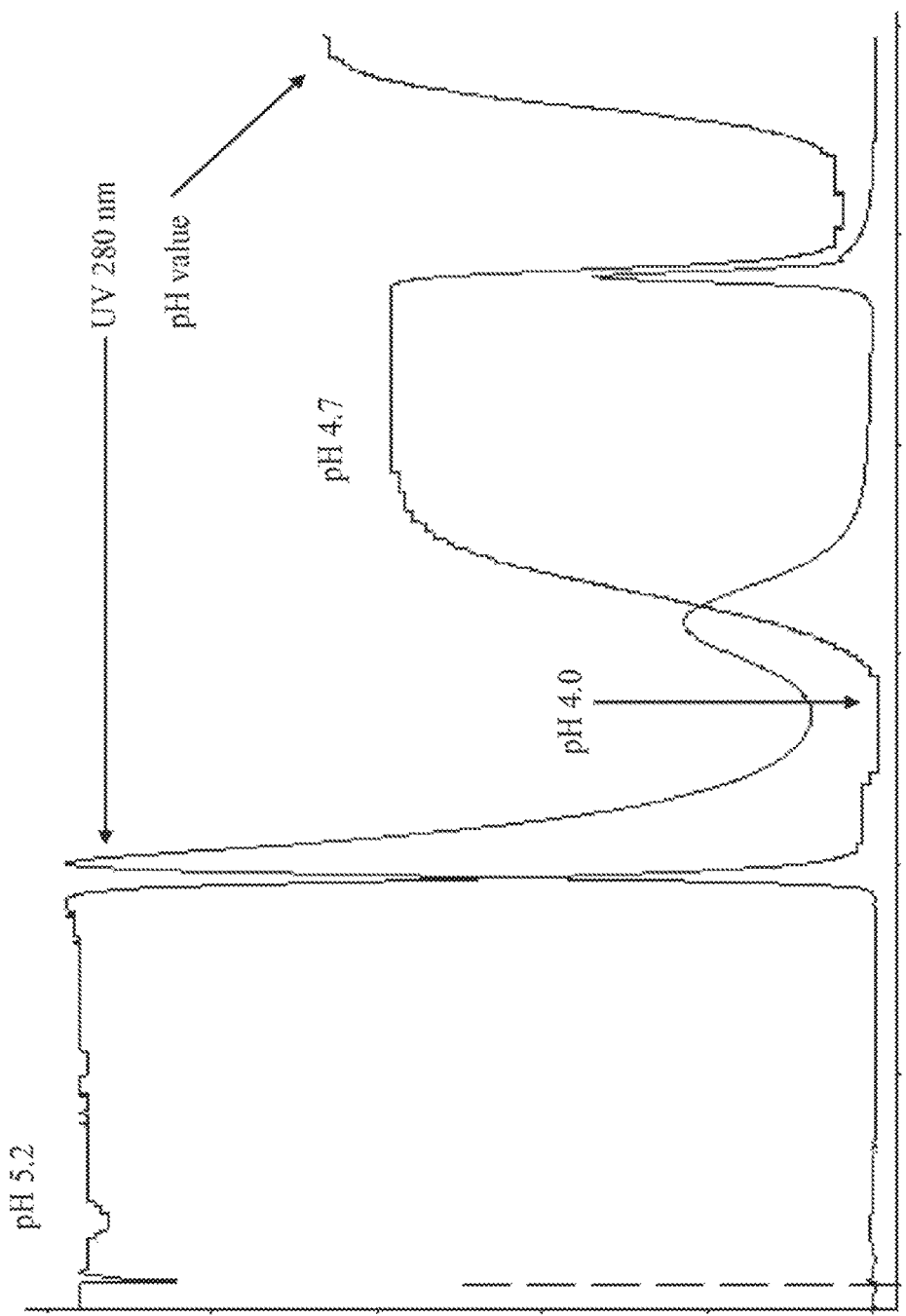
FIG. 1 Exemplary elution profile of mutIL15-Fc from CM-Sepharose FF at pH 5.2, 200 mmol/l NaCl: 4 mg mutIL15-Fc in 10 mmol/l sodium citrate pH 5.2 were loaded on a 5 ml HiTrap™ CM-Sepharose FF column; elution was done by step elution at 200 mmol/l NaCl in the same buffer. The yield of monomeric mutIL15-Fc in the first peak (pool) was 77%; the amount of aggregate in the pooled fractions was 2.2%; fractions of the second peak contained 30-90% aggregated mutIL15-Fc; tightly bound aggregates were eluted at 1 mol/l NaCl (3rd peak).

The term "recovery monomer" denotes the monomer found in the column efflux of the overall experiment and is calculated as the ratio of the monomer found in the total efflux vs. the monomer loaded onto the column.

The term "yield monomer" denotes the purified monomer eluted from the column in a quality worth to be further processed and is calculated as the ratio of the eluted and purified monomer vs. the monomer loaded onto the column.

The term "% monomer" denotes the partial fraction of mutIL15-Fc in monomeric form in the sample and is calculated as the ratio of monomeric mutIL15-Fc vs. the total amount of mutIL15-Fc, i.e. the sum of monomeric and aggregated form of the polypeptide, in the sample.

The Term "HMW" (=high molecular weight) denotes the aggregated form of the polypeptide.

Example 1

Production of mutIL15-Fc

The interleukin-15/Fc fusion protein has been prepared in accordance with the data and methods reported in the international patent applications WO 1997/041232, WO 2005/100394 and WO 2005/100395.

Example 2

Purification with a Protein A Affinity Chromatography

The crude cultivation supernatant obtained in Example 1 was applied to the protein A affinity chromatography material MabSelectSuRe (GE Healthcare, Uppsala, Sweden). The column was loaded with up to 14 mg protein per ml column volume. The bound mutIL15-Fc fusion protein was eluted with 100 mM citrate buffer at pH 3.6. An additional wash step prior to the elution was introduced to remove host cell DNA and host cell protein. Of from 76.6% to 78.4% mutIL15-Fc has been recovered from the protein A affinity chromatography material.

TABLE 1

Purification with a protein A affinity chromatography.

| load [mg/ml] | mode | elution with | recovery monomer | yield monomer | HMWs |
|---|---|---|---|---|---|
| up to 14 | bind-and-elute | 100 mM citrate buffer pH 3.6 | 76-78% | 73% | 35-40% |

Example 3

Purification with a Mixed-Mode Chromatography

The protein A purified mutIL15-Fc was adjusted to the required pH value and salt concentration by dialysis and/or adding of appropriate stock solutions and afterwards applied to the mixed-mode chromatography column previously equilibrated with 25 mM acetate buffer pH 5.5. As mixed-mode chromatography material Capto MMC has been used (GE Healthcare, Uppsala, Sweden). The column was loaded with up to 20 mg protein per ml column volume. A solution comprising 25 mM sodium phosphate at pH 6.5 was used for recovery of the protein from the column.

TABLE 2

Aggregate removal with a mixed-mode chromatography material.

| | HMW [%] | | | Total HMW | Monomer |
|---|---|---|---|---|---|
| | 1 | 2 | 3 | [%] | [%] |
| Load | 5.2 | 12.0 | 14.7 | 31.9 | 68.1 |
| Eluate (Pooled) | | 0.9 | 3.8 | 4.8 | 95.2 |
| Regenerate | 13.8 | 29.7 | 22.3 | 65.7 | 34.2 |

TABLE 3

HCP removal with a mixed-mode chromatography material.

| | HCP [ng/mg] |
|---|---|
| Load | 112 |
| wash | <1071 |
| pool | 23 |
| Regenerate | 202 |

The mutIL15-Fc recovery was 58.3%.

TABLE 4

Purification with a mixed-mode chromatography.

| loading buffer | load [mg/ml] | mode | elution with | yield monomer | monomer | HMWs |
|---|---|---|---|---|---|---|
| 25 mM acetate buffer pH 5.5 | up to 20 | bind-and-elute | 25 mM sodium phosphate pH 6.5 | 58% | 95% | 5% |

Example 4

Purification with a Hydrophobic Interaction Chromatography a) Phenyl Sepharose Protein A purified mutIL15-Fc (approx. 12 mg) was adjusted to the required salt and 2-propanol concentrations by the adding of appropriate stock solutions and applied to a Phenyl Sepharose column HP (GE Healthcare, Uppsala, Sweden) previously equilibrated with 20 mM Tris-HCl buffer comprising 1.5 mol/l NaCl and 10% (v/v) 2-propanol, pH 7.0. The applied solution contained approximately 30% aggregated protein. Removal of tightly bound protein was achieved with 100% 20 mM Tris-HCl buffer comprising 50% (v/v) 2-propanol, pH 7.0. The column was operated at a flow rate of 5 ml/min.

MutIL15-Fc was applied to the column in a 20 mM Tris-HCl buffer comprising 1.5 mol/l NaCl and 10% (v/v) 2-propanol, pH 7.0. Under these conditions mutIL15-Fc was found in the flow-through, whereas aggregates were bound to the chromatography material. In this non-binding method approx. 60% of the applied mutIL15-Fc monomer was recovered in the flow through at a purity of 94% with 6% aggregates.

TABLE 5

Purification with Phenyl Sepharose HP.

| loading buffer | load [mg/ml] | mode | elution with | yield monomer | monomer | HMWs |
|---|---|---|---|---|---|---|
| 20 mM Tris-HCl buffer, 1.5 mol/l NaCl, 10% (v/v) 2-propanol, pH 7.0 | 2.4 | flow-through | loading buffer (monomer), 20 mM Tris-HCl buffer, 50% (v/v) 2-propanol, pH 7.0 (aggregates) | 60% | 94% | 6% | b) Toyopearl Butyl

Protein A purified mutIL15-Fc (approx. 11 mg) was adjusted to the required salt and 2-propanol concentrations by the adding of appropriate stock solutions and applied to a Toyopearl Butyl-650M column (Tosoh Bioscience GmbH, Stuttgart, Germany) previously equilibrated with 20 mmol/l Tris/HCl pH 7.0, 0.5 mol/l NaCl, 15% (v/v) 2-propanol. The applied solution contained approximately 30% aggregated protein. Removal of tightly bound protein was achieved with 100% 20 mM Tris-HCl buffer comprising 50% (v/v) 2-propanol, pH 7.0. The column was operated at a flow rate of 5 ml/min.

When protein A purified mutIL15-Fc was loaded onto the column in 20 mmol/l Tris/HCl pH 7.0, 0.5 mol/l NaCl, 15% (v/v) 2-propanol 75% of monomeric mutIL15-Fc was recovered from the flow through at a purity of 95% with 5% of aggregates.

TABLE 6

Purification with Toyopearl Butyl-650M.

| loading buffer | load [mg/ml] | mode | elution with | yield monomer | monomer | HMWs |
|---|---|---|---|---|---|---|
| 20 mmol/l Tris/HCl pH 7.0, 0.5 mol/l NaCl, 15% (v/v) 2-propanol | 2.2 | flow-through | loading buffer (monomer), 20 mM Tris-HCl buffer, 50% (v/v) 2-propanol, pH 7.0 (aggregates) | 75% | 95% | 5% |

Example 5

Purification with a Weak Cation Exchange Chromatography a) Bind-and-Elute Mode

The recovered solution of a protein A affinity chromatography comprising the mutIL15-Fc was equilibrated in buffer A. This was either performed using Amicon Ultra 15 devices (30 kDa MWCO, Millipore, order no. UFC803096) or by diafiltration. The sample was applied to the CM-Sepharose FF column (GE Healthcare, Uppsala, Sweden) previously equilibrated with buffer A. Elution was either achieved in a gradient or in a step elution profile using buffer B. Columns were operated at 2 to 2.5 ml/min.

Using 10 mmol/l citrate buffer mutIL15-Fc bound completely to CM-Sepharose in the pH range from pH 3.0 to pH 5.4. At pH 5.5 about one third of the sample was recovered in the flow through. At pH 6.0 the main fraction of mutIL15-Fc did not bind to the CM-Sepharose. Therefore purification with CM-Sepharose in bind-and-elute mode was performed in the pH range between pH 5.0 and pH 5.5.

When using a linear salt gradient monomeric mutIL15-Fc eluted prior to aggregated mutIL15-Fc. The higher the pH value was the better the separation of monomeric and aggregated mutIL15-Fc was resulting in aggregate-free fractions in the first half of the elution peak at pH 5.0 or at pH 5.2.

When using step elution mutIL15-Fc was recovered with a 200 mmol/l sodium chloride solution. Using a 5 ml HiTrap column, mainly monomeric mutIL15-Fc (approx. 98% pure, yield 77%) eluted as a sharp peak followed by a second peak which contained aggregated mutIL15-Fc (approx. 90% aggregates) (see FIG. 1). Tightly bound protein was eluted with 1 mol/l NaCl. From the chromatogram it can be seen that during the elution of monomeric protein (first peak) the pH value decreased to approx. pH 4.0. During the elution of the second peak the pH partly recovered to pH 4.7. This shift in the pH value was also observed when the experiment was performed without loading of protein.

The timely separation of the monomer and aggregate peak can be improved with increasing column length of the column. For example, at pH 5.2 (10 mmol/l citrate) monomeric mutIL15-Fc was eluted from a 15 ml column at same purity (98%) and better yield (90%) in comparison to the 5 ml HiTrap column using 200 mmol/l NaCl. The column load in this experiment was less than 1 mg/ml column bed volume.

When the column load was stepwise increased the resolution of the CM-Sepharose FF column was gradually decreased. At low column load (0.36 mg per ml column bed volume, 10 mmol/l citrate pH 5.2) two totally separated peaks were eluted using a 200 mmol/l sodium chloride solution. At higher column load (5.3 mg/ml) the two peaks overlapped. The amount of aggregated mutIL15-Fc in the first (monomeric) peak was increased with increased amount of total protein. At low column load fractions of less than 3% aggregate could be recovered from the monomer peak. At higher load no fraction of the monomer peak contained less than 15% aggregates.

Best results were obtained with 210 mmol/l NaCl at pH 5.2 (81% yield, 98.5% purity). Changing the salt concentration only +/−10 mmol/l had an impact on the separation, resulting in a lower purity and/or yield. When the pH value of the loading buffer was changed +/−0.2 pH units the elution of monomeric mutIL15-Fc at 210 mmol/l NaCl led to a strong decrease in purity (>20% aggregates). At pH 5.0 230 mmol/l NaCl were necessary to recover purified mutIL15-Fc (98.6% pure) with moderate yield (58%). At pH 5.4 elution with NaCl concentrations of more than 150 mmol/l results in the elution of aggregates.

Alternatively to 10 mM citrate buffer pH 5.2 for column equilibration and protein loading 35 mmol/l acetate buffer at pH 5.0 or 10 mM MES buffer at pH 5.0 can be used, i.e. a buffer solution in the pH range of from pH 5.0 to pH 5.5 with a conductivity of about 1.9 mS/cm (same conductivity as the citrate buffer). For example with 35 mM acetate buffer, pH 5.0, mutIL15-Fc eluted in two separate peaks, where the first peak contained mainly monomeric protein (1%-8% aggregates) and the second peak contained mainly aggregates (60%-95%).

Using KCl instead of NaCl for the step elution method at 180 mmol/l KCl resulted in a better separation than NaCl. With 180 mmol/l KCl a monomer shoulder in the rising edge of the elution peak was seen whereas no peak separation was seen with 180 mmol/l NaCl. The use of 220 mmol/l NaCl resulted in a good separation of monomer (100% purity, 70% yield).

Using a pH gradient with acetate buffer and a gradient from pH 5.0 (buffer A) to pH 6.5 (buffer B), monomers eluted prior to aggregates. The shallower the gradient was the better the separation of monomer from aggregate was. The binding of mutIL15-Fc was complete at pH 5.0. Best purification results were obtained when equilibration and loading was performed at pH 5.0 and elution with 10% buffer B pH 6.0 (resulting in approx. pH 5.3 at the elution peak maximum). The main peak contained 68% of the loaded monomeric mutIL15-Fc at a purity of 99.5%. The column load was 0.3 mg/ml column bed volume. When the chromatography conditions were changed only slightly the purification of monomeric protein became worse again: when elution was performed at 11% buffer B, only 64% monomer at a purity of 97.5% could be recovered.

Using MES buffer at pH 5.0 and pH 8.0 for buffer A and B, respectively, at 60% buffer B step (approx. pH 5.8) a monomer peak of 98.5% purity and a monomer yield of 96% was obtained. The influence of the column load on purification quality is summarized in the following table.

TABLE 7

Influence of column load on yield and purity of mutIL15-Fc monomer from CM-Sepharose FF using a pH gradient with MES.

| run | column load [mg/ml] | aggregates input [%] | yield monomer [%] | HMWs [%] |
| --- | --- | --- | --- | --- |
| 1 | 0.3 | 40 | 96 | 1.5 |
| 2 | 3.1 | 40 | 75 | 2.0 |
| 3 | 10 | 38 | 76 | 4.5 |
| 4 | 7 | 4.5 | 80 | 1.0 |

Comparative separation experiments performed with Toyopearl CM-650M (Tosoh Bioscience GmbH, Stuttgart, Germany, order no. 43203) provided for similar results as those obtained with the CM-Sepharose FF column.

TABLE 8

Purification with CM-Sepharose FF in bind-and-elute mode.

| loading buffer | load [mg/ml] | mode | elution with | recovery monomer | yield monomer | HMWs | comment |
| --- | --- | --- | --- | --- | --- | --- | --- |
| 40 mM sodium acetate, pH 5.3 | 0.4 | bind-and-elute | 200 mM sodium chloride | 73% | 73% | 25% | |
| 25 mM sodium acetate, pH 5.2 | 5 | bind-and-elute | 7.5 mM sodium acetate, 200 mM sodium chloride, pH 5.5 | 84% | 48% | 0% | 24% aggregate free, monomer in flow-through |
| 10 mM sodium acetate, pH 5.5 | 1 | bind-and-elute | 200 mM sodium chloride | 72% | 51% | 0% | |
| 15 mM sodium acetate, pH 5.5 | 0.8 | bind-and-elute | 200 mM sodium chloride | 77% | 68% | 3% | |
| 20 mM sodium acetate, pH 5.5 | 0.6 | bind-and-elute | 200 mM sodium chloride | 96% | 88% | 14% | |

TABLE 8-continued

Purification with CM-Sepharose FF in bind-and-elute mode.

| loading buffer | load [mg/ml] | mode | elution with | recovery monomer | yield monomer | HMWs | comment |
|---|---|---|---|---|---|---|---|
| 25 mM sodium acetate, pH 5.5 | 0.6 | bind-and-elute | 200 mM sodium chloride | 90% | 90% | 22% | |
| 30 mM sodium acetate, pH 5.5 | 0.7 | bind-and-elute | 200 mM sodium chloride | 69% | 62% | 27% | 7% aggregate free, monomer in flow-through |
| 60 mM sodium acetate, pH 5.1 | 11 | bind-and-elute | 200 mM sodium chloride | 95% | 93% | 27% | |
| 90 mM sodium acetate, pH 5.1 | 14 | bind-and-elute | 200 mM sodium chloride | 91% | 85% | 21% | |
| 10 mmol/l sodium citrate, pH 5.0 | 5.6 | bind-and-elute | 220 mM sodium chloride | | n.d. | >20% | |
| 10 mmol/l sodium citrate, pH 5.0 | 3 | bind-and-elute | 230 mM sodium chloride | | 58% | 1.4% | |
| 10 mmol/l sodium citrate, pH 5.0 | 3 | bind-and-elute | 240 mM sodium chloride | | 51% | 2% | |
| 10 mmol/l sodium citrate, pH 5.2 | 4.2 | bind-and-elute | 200 mM sodium chloride | | n.d. | >5% | |
| 10 mmol/l sodium citrate, pH 5.2 | 3.5 | bind-and-elute | 210 mM sodium chloride | | 81% | 1.5% | |
| 10 mmol/l sodium citrate, pH 5.2 | 3.4 | bind-and-elute | 220 mM sodium chloride | | 70% | 1.5% | |
| 10 mmol/l sodium citrate, pH 5.4 | 2 | bind-and-elute | 130 mM sodium chloride | | n.d. | >5% | |
| 10 mmol/l sodium citrate, pH 5.4 | 1 | bind-and-elute | 150 mM sodium chloride | | n.d. | 4% | |
| 10 mmol/l sodium citrate, pH 5.4 | 2.5 | bind-and-elute | 200 mM sodium chloride | | n.d. | >23% | | b) Flow-Through Mode

The solution was dialyzed against the respective loading buffer as listed in the following table. The monomeric mutIL15-Fc fusion protein was recovered in the flow-through in the loading buffer (isocratic elution). Aggregates and fragments were recovered with a single step elution with a solution comprising 200 mM sodium chloride.

TABLE 9

Purification with CM-Sepharose FF in flow-through mode.

| loading buffer | load [mg/ml] | mode | recovery monomer | yield monomer | HMWs | comment |
|---|---|---|---|---|---|---|
| 50 mM sodium acetate, pH 5.3 | 0.6 | flow-through | 88% | 27% | 0% | |

TABLE 9-continued

Purification with CM-Sepharose FF in flow-through mode.

| loading buffer | load [mg/ml] | mode | recovery monomer | yield monomer | HMWs | comment |
|---|---|---|---|---|---|---|
| 55 mM sodium acetate, pH 5.3 | 0.4 | flow-through | 71% | 13% | 0% | |
| 60 mM sodium acetate, pH 5.3 | 0.4/0.55/ 1.4/11 | flow-through | 86/79/ 94/85% | 10/33/ 29/53% | 0/0/ 0/1% | |
| 70 mM sodium acetate, pH 5.3 | 0.55/1.4/ 12 | flow-through | 83/80/ 86% | 72/58/ 42% | 0/0/ 3% | |
| 85 mM sodium acetate, pH 5.3 | 0.5/3/11 | flow-through | 75/95/87% | 64/80/76% | 0/5/18% | |
| 100 mM sodium acetate, pH 5.3 | 0.3/0.55/ 1.5 | flow-through | 88/82/ 91% | 85/72/ 81% | 2/7/ 11% | |
| 40 mM sodium acetate, pH 5.5 | 0.6 | flow-through | 76% | 57% | 0% | monomer also bound (approx. 20%) |
| 50 mM sodium acetate, pH 5.5 | 0.6 | flow-through | 77-84% | 67-71% | 3-5% | monomer also bound (<20%) |
| 55 mM sodium acetate, pH 5.5 | 0.5 | flow-through | 74% | 68% | 4% | |
| 60 mM sodium acetate, pH 5.5 | 0.4 | flow-through | 68% | 62% | 6% | |
| 65 mM sodium acetate, pH 5.5 | 0.6 | flow-through | 101% | 86% | 10% | |
| 70 mM sodium acetate, pH 5.5 | 0.6 | flow-through | 81% | 76% | 10% | |
| 100 mM sodium acetate, pH 5.5 | 1.6 | flow-through | 117% | 104% | 23% | |
| 40 mM sodium acetate, pH 5.7 | 0.4 | flow-through | 75% | 71% | 7% | |
| 50 mM sodium acetate, pH 5.7 | 0.5 | flow-through | 84-90% | 78-87% | 13-17% | |
| 55 mM sodium acetate, pH 5.7 | 0.4 | flow-through | 77% | 73% | 19% | |
| 60 mM sodium acetate, pH 5.7 | 0.4 | flow-through | 69% | 68% | 12% | |
| 10 mM sodium acetate, pH 6 | 1 | flow-through | 97% | 55% | 0% | |
| 15 mM sodium acetate, pH 6 | 0.8 | flow-through | 89% | 79% | 17% | |

TABLE 9-continued

Purification with CM-Sepharose FF in flow-through mode.

| loading buffer | load [mg/ml] | mode | recovery monomer | yield monomer | HMWs | comment |
|---|---|---|---|---|---|---|
| 25 mM sodium acetate, pH 6 | 0.8 | flow-through | 78% | 78% | 21% | |
| 50 mM sodium acetate, pH 6 | 0.8 | flow-through | 79% | 79% | 26% | |
| 100 mM sodium acetate, pH 6 | 1.6 | flow-through | 123% | 118% | 35% | |
| 10 mM potassium phosphate, pH 7 | 0.5 | flow-through | 91% | 91% | 37% | |
| 100 mM sodium acetate, 50 mM Tris, pH 7 | 1.6 | flow-through | 114% | 114% | 39% | monomer also bound (approx. 20%) |
| 100 mM sodium acetate, pH 5.1 | 11 | flow-through | 90% | 43% | 1% | |
| 110 mM sodium acetate, pH 5.1 | 13 | flow-through | 108% | 73% | 3% | |
| 120 mM sodium acetate, pH 5.1 | 13 | flow-through | 99% | 70% | 1% | |
| 60 mM sodium acetate, pH 5.3 | 11 | flow-through | 85% | 53% | 1% | |
| 85 mM sodium acetate, pH 5.3 | 11 | flow-through | 87% | 76% | 18% | |

Example 6

Purification with a Strong Cation Exchange Chromatography

Prior to loading the column mutIL15-Fc was equilibrated in 10 mmol/l sodium citrate pH 5.0, 5.2 and 5.5, respectively, by dialysis. After the loading elution was either achieved in an increasing salt gradient or in a step elution profile using the equilibration buffer supplemented with 1 mol/l NaCl. Columns were operated at 2 ml/min.

The mutIL15-Fc bound completely to SP-Sepharose FF (GE Healthcare, Uppsala, Sweden) at pH 5.0, 5.2 and 5.5 as well as to Toyopearl SP-650 M (Tosoh Bioscience GmbH, Stuttgart, Germany, order no. 43202) at pH 5.2. Elution of mutIL15-Fc started during re-equilibration of the column after end of load and before starting the salt gradient. In the main peak, monomeric mutIL15-Fc eluted earlier than aggregated protein, but with a total overlap not allowing significant separation of the monomeric form from the aggregates, independent of media, pH and elution conditions used.

TABLE 10

Purification with sulfopropyl media.

| material | loading buffer | load [mg/ml] | mode | elution with | HMWs in the main peak from . . . to |
|---|---|---|---|---|---|
| Sepharose | 10 mmol/l sodium citrate pH 5.0 | approx. 0.4 | bind-and-elute | loading buffer, linear gradient from 0 . . . 1 mol/l NaCl | 2 to 46% |
| Sepharose | 10 mmol/l sodium citrate pH 5.0 | approx. 0.4 | bind-and-elute | loading buffer, elution step with 0.15 mol/l NaCl | 0 to 17% |
| Sepharose | 10 mmol/l sodium citrate pH 5.0 | approx. 0.4 | bind-and-elute | loading buffer, elution step with 0.12 mol/l NaCl | 1 to 10% |
| Sepharose | 10 mmol/l sodium citrate pH 5.2 | approx. 0.4 | bind-and-elute | loading buffer, elution step with 0.15 mol/l NaCl | 4 to 11% |
| Toyopearl | 10 mmol/l sodium citrate pH 5.2 | approx. 0.4 | bind-and-elute | loading buffer, linear gradient from 0 . . . 1 mol/l NaCl | 0 to 14% |

TABLE 10-continued

Purification with sulfopropyl media.

| material | loading buffer | load [mg/ml] | mode | elution with | HMWs in the main peak from ... to |
|---|---|---|---|---|---|
| Toyopearl | 10 mmol/l sodium citrate pH 5.2 | approx. 0.4 | bind-and-elute | loading buffer, elution step with 0.12 mol/l NaCl | 0 to 12% |
| Sepharose | 10 mmol/l sodium citrate pH 5.5 | approx. 0.4 | bind-and-elute | loading buffer, elution step with 0.15 mol/l NaCl | 9 to 30% |

Example 7

Purification with Protein A Chromatography, Size Exclusion Chromatography, and Carboxymethyl Sepharose The crude cultivation supernatant obtained in Example 1 was applied to the protein A affinity chromatography material MabSelectXtra (GE Healthcare, Uppsala, Sweden). The column was loaded with about 12 mg protein per ml column volume. The bound mutIL15-Fc fusion protein was eluted with 100 mM sodium acetate buffer at pH 3.2. An additional wash step prior to the elution was introduced to remove host cell DNA and host cell protein. About 80% mutIL15-Fc has been recovered.

The protein A purified mutIL15-Fc was further purified using SEC. The recovered pooled monomer containing fractions contained approx. 95.5% purity (4.5% aggregates).

For the carboxymethyl sepharose chromatography a MES buffer system with a pH gradient (pH 5.0/pH 8.0) as reported in Example 5 was used.

Figure 2:
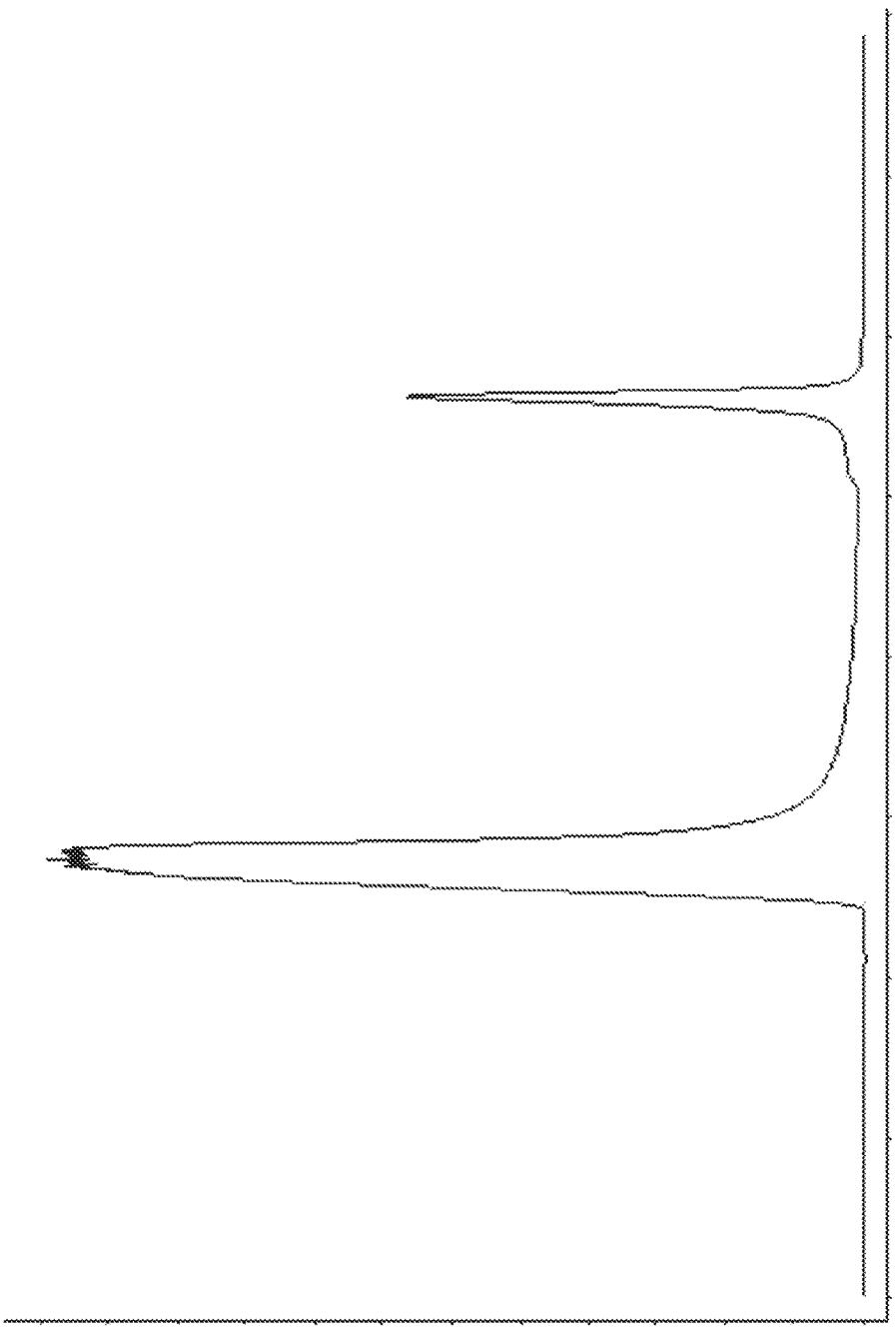
FIG. 2 Exemplary elution profile of mutIL15-Fc from CM-Sepharose FF in the MES buffer system (pH 5.0/pH 8.0): mutIL15-Fc previously purified to 95.5% monomer purity was loaded onto the CM-Sepharose FF column at pH 5.0; elution was initiated by increasing the pH (60% buffer B step, approx. pH 5.8); the yield of monomeric mutIL15-Fc in the first peak (pool) was 80%. The amount of aggregate in the pooled fractions was lowered to 1%; fractions of the second peak contained approx. 20% aggregated mutIL15-Fc.

As shown in FIG. 2 and summarized in Table 11 mutIL15-Fc was obtained with high purity when a moderately aggregated sample was loaded onto the column. Even at a relatively high column load of 7 mg/ml 99% pure monomer could be recovered at a yield of 80%.

TABLE 11

Purification of pre-purified sample with CM-Sepharose FF

| loading buffer | load [mg/ml] | mode | elution with | yield monomer | HMWs |
|---|---|---|---|---|---|
| 180 mmol/l MES, pH 5.0 (=buffer A) | 7 | bind-and-elute, pH gradient | 60% step gradient with buffer B = 30 mmol/l MES, pH 8.0 | 80% | 1% |

Example 8

Figure 3A:
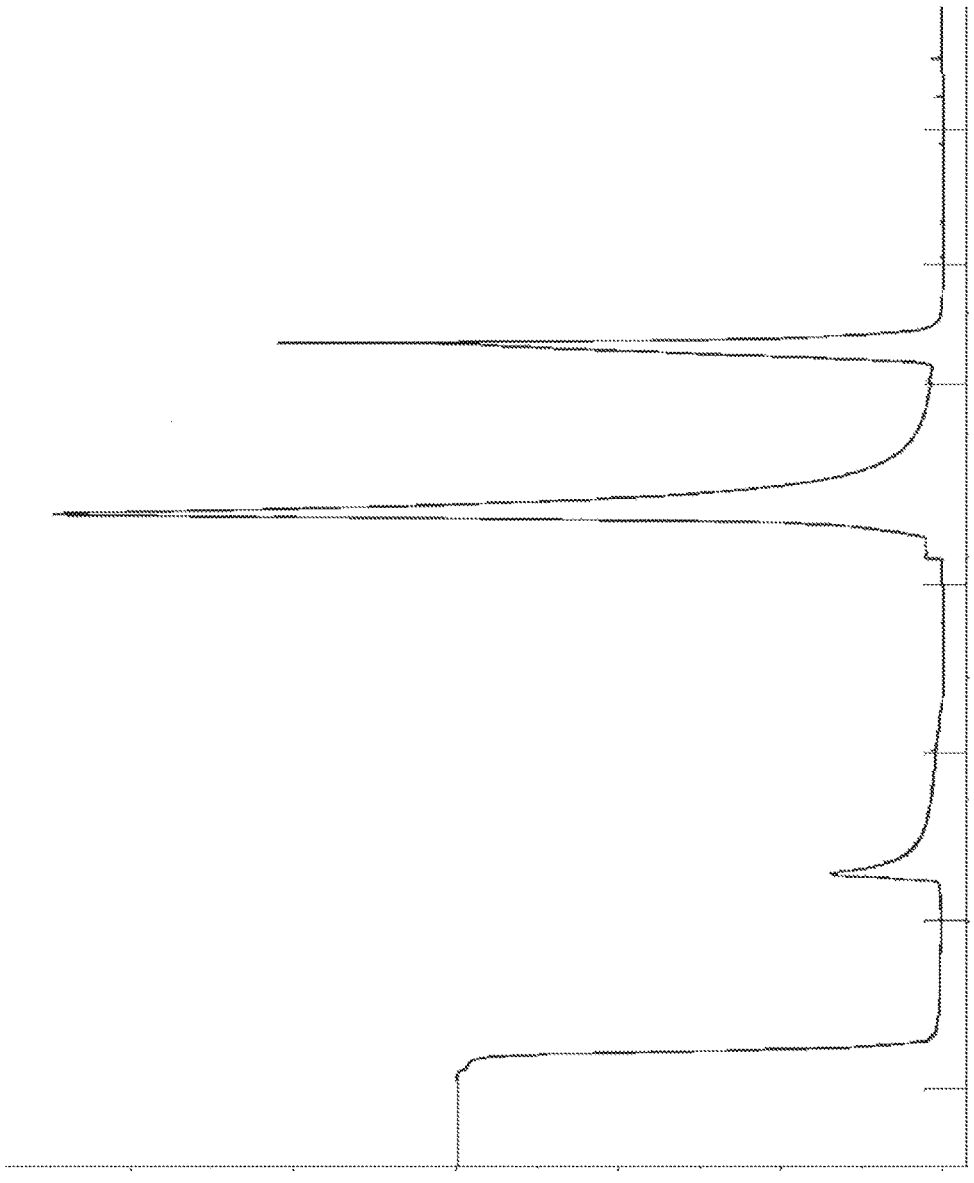

Purification with Protein A Chromatography, a Mixed-Mode Chromatography, and Carboxymethyl-Sepharose The crude cultivation supernatant obtained in Example 1 was applied to the protein A affinity chromatography material MabSelectSuRe (GE Healthcare, Uppsala, Sweden). The column was loaded with up to 14 mg protein per ml column volume. The bound mutIL15-Fe fusion protein was eluted with 100 mM citrate buffer at pH 3.6. An additional wash step prior to the elution was introduced to remove host cell DNA and host cell protein. Of from 76.6% to 78.4% mutIL15-Fc has been recovered (FIG. 3a) from the protein A affinity chromatography material.

Figure 3B:
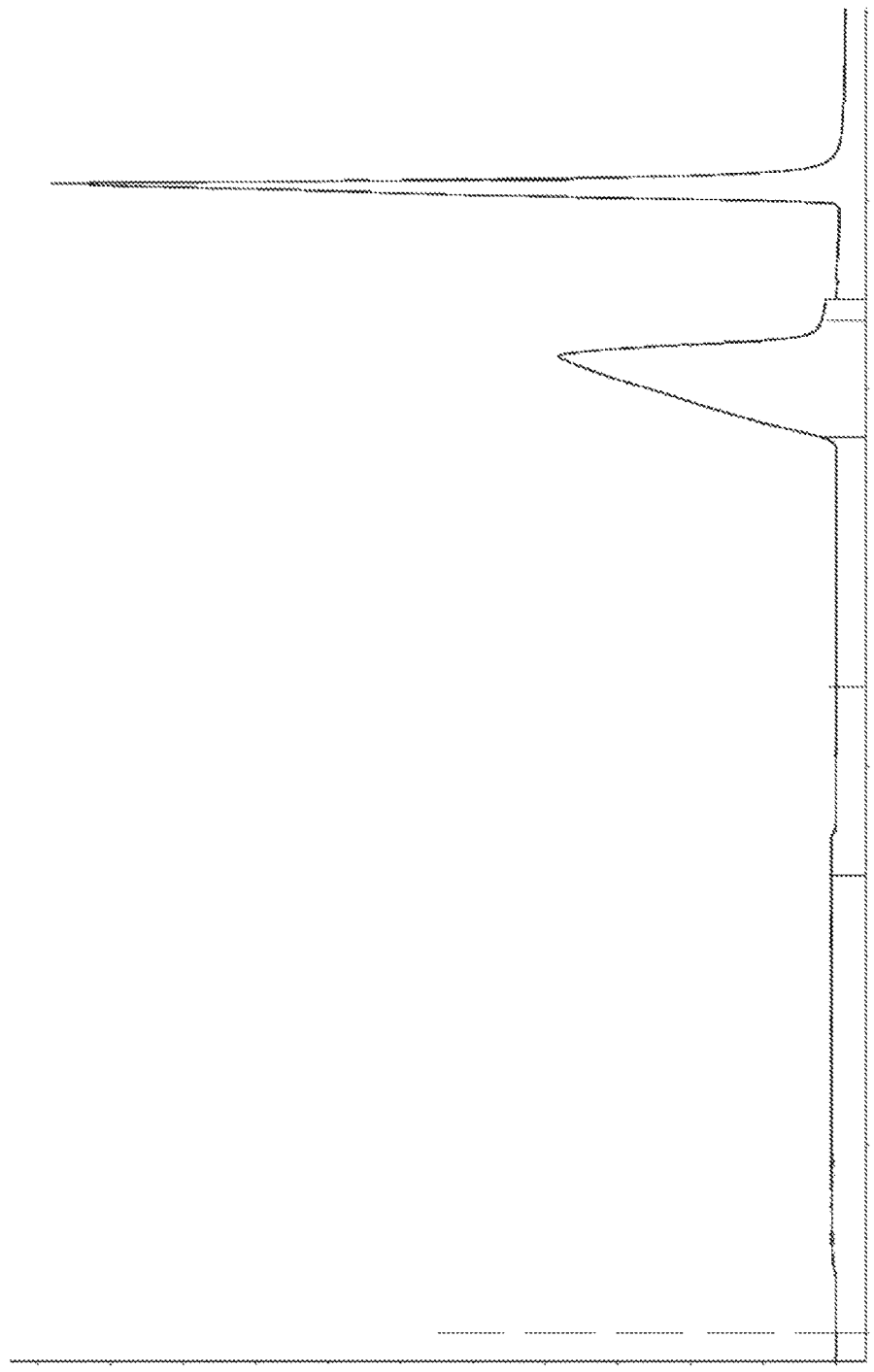

The protein A purified mutIL15-Fc was adjusted to the required pH value and salt concentration by dialysis and/or adding of appropriate stock solutions and afterwards applied to the mixed-mode chromatography column previously equilibrated with 25 mM acetate buffer pH 5.5. As mixed-mode chromatography material Capto MMC has been used (GE Healthcare, Uppsala, Sweden). The column was loaded with up to 20 mg protein per ml column volume. A solution comprising 25 mM sodium phosphate at pH 6.5 was used for recovery of the protein from the column (FIG. 3b).

The Capto MMC eluate was dialyzed against 75 mM sodium acetate buffer pH 5.3. The CM-Sepharose column was loaded with up to 5 mg protein per ml column volume. The monomeric mutIL15-Fc fusion protein was recovered in the flow-through in the loading step. Aggregates and fragments were recovered with a single step elution with a solution comprising 200 mM sodium chloride (FIG. 3c). The aggregate removal capacity of the CM-Sepharose chromatography performed under the conditions described here is shown in Table 12. The yield of mutIL15-Fc is about 81% in this step.

TABLE 12

Aggregate removal by CM Sepharose chromatography in flow-through mode as third chromatography step after affinity and mixed-mode chromatography

|  | HMW | monomer | LMW |
|---|---|---|---|
| Load | 6.70 | 91.67 | 1.63 |
| Pool | 1.80 | 97.31 | 0.89 |
| Regenerate | 20.45 | 67.39 | 12.15 |

The invention claimed is:

1. A method for removing aggregates from a solution with high aggregate content, comprising the steps of:
   a) applying a solution comprising the polypeptide in monomeric form and in aggregated form, wherein the aggregated form is 20% or more as determined by size exclusion chromatography of the total. polypeptide in the solution, to a mixed-mode Chromatography material. and recovering the polypeptide from the mixed-mode chromatography material, wherein the polypeptide recovered from the mixed-mode chromatography material has a reduced aggregate content; and
   b) applying the solution obtained in the previous step to a weak cation exchange chromatography material and recovering the polypeptide therefrom and thereby producing the monomeric polypeptide,
   wherein the solution applied to the mixed-mode chromatography material and/or the weak cation exchange chromatography material has a pH value at least 0.2 pH units and at most 2.5 pH units above the isoelectric point of the polypeptide.

2. The method according to claim 1, characterized in that the solution applied to the mixed-mode chromatography material and/or the weak cation exchange chromatography material is a buffered solution with a buffer concentration of from about 1 mmol/l to about 150 mmol/l.

3. The method according to claim 2, characterized in that the buffer is selected from citrate buffer, acetate buffer and MES buffer.

4. The method according to claim 1, characterized in that the recovering from the weak cation exchange chromatography material is from the eluate of the weak cation exchange chromatography material or from the flow-through of the weak cation exchange chromatography material.

5. The method according to claim 1, characterized in that the applying to and recovering from the mixed-mode chromatography material comprises the following steps
   applying to the mixed-mode chromatography material a solution comprising a buffer with a pH value of the IEP of the polypeptide plus about 0.7 pH units to about 1.3 pH units,
   adjusting the solution comprising the polypeptide prior to the applying to the chromatography material to a pH value of the IEP of the polypeptide plus about 0.7 pH units to about 1.3 pH units,
   applying the solution comprising the polypeptide to the mixed-mode chromatography material,
   recovering the polypeptide from the mixed-mode chromatography material by applying a solution comprising a phosphate buffer with a pH value of the IEP of the polypeptide plus about 1.7 pH units to about 2.3 pH units.

6. The method according to claim 5, characterized in that the mixed-mode chromatography buffer has a conductivity of about 1.9 mS/cm.

7. The method according to claim 1, characterized in that the applying to the weak cation exchange chromatography material and the recovering of the polypeptide comprises the following steps
- applying to the weak cation exchange chromatography material a solution comprising a buffer with a pH value of the IEP of the polypeptide plus about 0.2 pH units to about 1.0 pH units,
- adjusting the solution comprising the polypeptide prior to the applying to the chromatography material to a pH value of the IEP of the polypeptide plus about 0.2 pH units to about 1.0 pH units,
- applying the solution comprising the polypeptide to the weak cation exchange chromatography material,
- recovering the polypeptide from the weak cation exchange chromatography material by applying a solution comprising sodium chloride or potassium chloride at a concentration of from about 210 mmol/l to about 240 mmol/l, or
- recovering the polypeptide from the weak cation exchange chromatography material with a solution of a pH value of from about pH 6.0 to about pH 8.0.

8. The method according to claim 7, characterized in that in the recovering the pH value is about pH 5.0 and the sodium chloride concentration is about 230 mmol/l, or the pH value is about pH 5.2 and the sodium chloride concentration is about 210 mmol/l.

9. The method according to claim 7, characterized in that the recovering is by an isocratic elution.

10. The method according to claim 7, characterized in that the recovering is by adding 10% (v/v) of an acetate buffer of a pH value of from about pH 6.0 to about pH 6.5 or the recovering is by adding 60% (v/v) of a MES buffer of a pH value of about pH 8.0.

11. The method according to claim 1, characterized in that the applying to the weak cation exchange chromatography material and the recovering of the polypeptide comprises the following steps
- applying to the weak cation exchange chromatography material a solution with a pH value of the IEP of the polypeptide plus about 0.2 pH units to about 1.2 pH units,
- adjusting the solution comprising the polypeptide prior to the applying to the chromatography material to a pH value of the IEP of the polypeptide plus about 0.2 pH units to about 1.2 pH units,
- applying the solution to a weak cation exchange chromatography material,
- recovering the polypeptide from the flow-through.

12. The method according to claim 11, characterized in that the adjusting is to an acetate buffer of about pH 5.1 and of from about 100 mol/l to about 120 mmol/l, or to an acetate buffer of about pH 5.5 and of about 40 mmol/l to about 55 mmol/l, or to an acetate buffer of about pH 6.0 and of about 10 mmol/l.

13. The method according to claim 11, characterized in that the buffer in step a) is an acetate buffer of about pH 5.3 and of about 50 mmol/l to about 75 mmol/l, or an acetate buffer of about pH 5.5 and of about 7.5 mmol/l to about 15 mmol/l.

* * * * *